(12) United States Patent
Hawes et al.

(10) Patent No.: US 7,351,333 B2
(45) Date of Patent: Apr. 1, 2008

(54) CENTRIFUGE

(75) Inventors: David W. Hawes, Uxbridge (GB); Lee Janaway, Uxbridge (GB); Ian A. Sutherland, Uxbridge (GB); Philip L. Wood, Uxbridge (GB)

(73) Assignee: Brunel University, Middlesex (GB)

( * ) Notice: Subject to any disclaimer, the term of this patent is extended or adjusted under 35 U.S.C. 154(b) by 337 days.

(21) Appl. No.: 10/958,173

(22) Filed: Oct. 4, 2004

(65) Prior Publication Data

US 2005/0109686 A1  May 26, 2005

Related U.S. Application Data

(63) Continuation of application No. PCT/GB03/01502, filed on Apr. 7, 2003.

(30) Foreign Application Priority Data

| Apr. 5, 2002 | (GB) | ................................ 0207959.8 |
| Apr. 5, 2002 | (GB) | ................................ 0207961.4 |
| Apr. 5, 2002 | (GB) | ................................ 0207962.2 |
| Apr. 5, 2002 | (GB) | ................................ 0207963.0 |

(51) Int. Cl.
*B01D 15/08* (2006.01)

(52) U.S. Cl. .................................... 210/198.2; 210/657

(58) Field of Classification Search ............. 210/360.1, 210/635, 656, 657, 198.2, 198.3
See application file for complete search history.

(56) References Cited

U.S. PATENT DOCUMENTS 3,420,436 A * 1/1969 Ito ................................ 494/47

(Continued)

FOREIGN PATENT DOCUMENTS

GB    2034197    6/1980

(Continued)

*Primary Examiner*—Ernest G. Therkorn
(74) *Attorney, Agent, or Firm*—Darby & Darby

(57) ABSTRACT

A centrifuge (10) is provided with a cantilevered shaft (18) upon which the main drive rotor (26) is located. A bobbin (62) is attached to the planetary gear shaft (44), which is driven in planetary motion by the rotation of the rotor (26) and its toothed engagement with the shaft (18) of the cantilevered rotor. A flying lead section (72) extends from the bobbin (62) through an aperture in the cantilevered rotor (26). The arrangement provides a centrifuge structure which can handle higher rotational speeds while maintaining resolution. The flying lead section (72) provides a simple path for the inlet and outlet leads (84,86) which reduces dead volume and increases reliability. The bobbin (62) supports at least one coil (68). Rotor component (44) includes at least one bearing (50, 52). Attachment means (66) are provided removably to attach the bobbin (62) to the rotor component (44), the attachment means (66) enabling removal of the bobbin (62) from the rotor without removal of the or any bearing (50, 52) of the rotor component (44). In the preferred embodiment, the attachment means (66) removably attaches the bobbin (62) to an end of the rotor component (44). A gear assembly (40) for the centrifuge (10) is enclosed in a chamber (56) of a rotor (26), which chamber (56) can be provided with lubricant. A chromatography coil assembly is formed from a plurality of rigid substrates (10, 12) which are disc-shaped in plan view. Produced within each substrate (10, 12) is a channel (14, 16) which is closed by the lower surface of the substrate lying thereon, as shown in relation to channel (14). A coupling conduit couples the two channels (14, 16) together to form a unitary coil.

10 Claims, 4 Drawing Sheets

U.S. PATENT DOCUMENTS

| | | | | |
|---|---|---|---|---|
| 3,994,805 A | * | 11/1976 | Ito | 210/635 |
| 4,082,217 A | | 4/1978 | Westberg | |
| 4,111,356 A | | 9/1978 | Boggs et al. | |
| 5,024,758 A | * | 6/1991 | Ito | 210/198.2 |
| 5,169,521 A | * | 12/1992 | Oka et al. | 210/198.2 |
| 5,217,608 A | * | 6/1993 | Conway | 210/198.2 |
| 6,372,142 B1 | * | 4/2002 | Gjerde et al. | 210/635 |
| 6,464,882 B1 | * | 10/2002 | Prior et al. | 210/657 |
| 2001/0042714 A1 | * | 11/2001 | Gjerde et al. | 210/634 |
| 2002/0153312 A1 | * | 10/2002 | Gjerde et al. | 210/635 |

FOREIGN PATENT DOCUMENTS

| | | |
|---|---|---|
| JP | 11-183455 | 7/1999 |
| RU | 2084263 | 7/1997 |

* cited by examiner

CENTRIFUGE

This application is a continuation of PCT International Application NO. PCT/GB03/01502, filed Apr. 7, 2003, and claims the benefit of British Patent Application Nos. 0207959.8, filed Apr. 5, 2002, 0207961.4, filed Apr. 5, 2002, 0207962.2, filed Apr. 5, 2002, and 0207963.0, filed Apr. 5, 2002 which are incorporated by reference herein. The International Application was published in English on Oct. 23, 2003 as WO 03/086639 A2 under PCT Article 21(2).

FIELD AND BACKGROUND OF THE INVENTION

The present invention relates to centrifuge apparatus.

Although it has been some time since the introduction of counter current chromatography instruments, these still remain in their infancy. One of the major factors restricting the use of counter current chromatography as an analytical tool is the speed at which a separation may be conducted. Another problem in the development of such instruments has been the inability to interface directly to a mass spectrometer detector without using a splitter.

For example, a prior art instrument with a coil of 350 ml capacity and internal diameter of 1.6 mm, is typically operated at a fluid flow of 2 ml per minute. With this structure, the separation time is approximately 3 hours. This does not provide a sufficiently fast separation for such an instrument to be of significant commercial use.

It is desirable to reduce both coil capacity (so that less sample material is required) and to reduce separation time. Capacity can be reduced by reducing the internal diameter of the coil. For example, there have been attempts to provide 90 ml capacity coils with internal diameter of 0.8 mm while retaining the same linear fluid flow by having a fluid flow rate of 0.5 ml per minute. Separation time can be reduced by reducing the length of the coil but so doing has led to the loss of resolution. For example, reducing the coil length by a factor of four to reduce capacity to 22.5 ml and separation time down to 45 minutes has only been achievable with a halving of resolution, which is not acceptable.

In addition, centrifuges for counter current chromatography typically have one or more coils of tubing of substantial length (many metres) wound onto one or more bobbins. The bobbins are rotated at high speeds, typically over 1,000 rpm. The sample to be separated is passed through the tubing during centrifuging, that is during rotation of the coils, which rotation causes the separation. A detector, typically UV but preferably a mass spectrometer, is provided to analyse the outlet fluid stream.

The conventional coil structures present several difficulties in the design and operation of such centrifuges. For example, the tubing tends to move and to unwind during operation of the machine. Although fixing mechanisms such as channels for holding each winding of tubing individually and the use of potting compounds to hold the coils have been used, these do not always prevent the problems and also add complexity and in some cases weight to the machine. Furthermore, the design of the coil winding tends to be limited to a simple helix arrangement.

SUMMARY OF THE INVENTION

The present invention seeks to provide an improved new centrifuge, preferably of a type which can be used to conduct counter current chromatography.

The invention also provides for counter current chromatograph apparatus including a centrifuge as specified herein.

According to another aspect of the present invention, there is provided a centrifuge lead assembly for a centrifuge including inlet and outlet leads and a flying lead section provided with a sheath within which a portion of the inlet and outlet leads is located.

According to another aspect of the present invention, there is provided a centrifuge bobbin assembly including a bobbin for supporting at least one coil; a rotor component for imparting rotation to the bobbin and including at least one bearing; and attachment means operable removably to attach the bobbin to the rotor component, the attachment means enabling removal of the bobbin from the rotor without removal of the or any bearing of the rotor component.

According to another aspect of the present invention, there is provided a centrifuge bobbin assembly including a bobbin for supporting at least one coil; a rotor component for imparting rotation to the bobbin; and attachment means operable removably to attach the bobbin to an end of the rotor component.

According to another aspect of the present invention, there is provided a centrifuge assembly including coil rotation means operable to impart rotation to a coil and a housing substantially enveloping the coil rotation means.

According to another aspect of the present invention, there is provided a chromatography coil assembly including a substantially rigid substrate and at least one conduit formed by a plurality of walls, at least one of which walls being formed in the substrate. Preferably, there is provided a plurality of substrates in overlying relation to one another, adjoining substrates providing all the walls of a conduit such that the conduit is formed by the substrates themselves and not by any other device.

The preferred embodiments can provide a coil structure which is rigid and solid, enabling the coil to be rotated at very high speeds much in excess of 2000 rpm without risk of deformation of the coil structure. It also allows the provision of coils with substantially lower coil volume than with conventional tube coils, or coils with much higher coil volume if desired. The assembly also allows for the provision of different coil forms and cross-sectional shapes, which is not readily achievable with prior art structures. The skilled person will appreciate from the following description that the assembly can provide many other benefits relative to prior art systems.

In arriving at the embodiments described herein, the inventors sought to devise an instrument which could perform separation in minutes, provide no or very limited back pressure build-up and good resolution. Considerations were to maintain stationary phase retention while reducing coil volume by shortening coil length but maintaining a higher linear velocity by increasing the speed of rotation of the coil to allow the mobile phase flow rate to be increased. In effect, this has been achieved by increasing the speed of rotation of the coil(s), the higher "g" fields produced during operation of the apparatus giving better retention of the stationary phase allowing a significant increase in flow without loss of retention. Furthermore, the preferred embodiments provide a smaller rotor which gives more mixing and settling steps per minute, leading to even better mass transfer between the phases and hence resolution.

An additional benefit found in the embodiments described herein is that coil and flying lead back pressure can be significantly reduced so that they can now accommodate the back pressure generated by, for example, a mass spectrometer detector nebuliser. A tested embodiment of the present invention had a coil capacity of 25 ml with 0.8 mm internal diameter coil tubing. It is possible to maintain a flow rate of 2 to 4 ml per minute, thereby achieving separation in 6 to 12 minutes. The coil capacity was reduced even further to 5 ml to reduce separation time to 1 to 2 minutes while maintaining good resolution. Thus, it is possible to provide true rapid analytical scale counter current chromatography.

In one embodiment, a coil with 0.8 mm internal diameter tubing around 10 metres long was used in the machine able to rotate at high rotational speeds, in excess of 2000 rpm, thus producing a higher "g" level. The effect was to preserve a high percentage stationary phase retention and to increase the number of mixing and settling cycles over a given time period. Both of these effects offset the reduced length of coil tubing.

The aspect of a cantilevered rotor provided in the machine enables all of the components of the centrifuge to be mounted on the cantilevered rotor and substantially reduced complexity of machine. It also allows the use of specific design features, such as the flying lead configuration, the bobbin configuration and also the enclosed gear box arrangement, all taught herein. It also allows the use of a different type of coil structure as disclosed herein.

The aspect of the arrangement of a flying lead section reduces to a minimum the number of torturous paths required to be taken by fluid exiting the coil and hence the corruption of the chromatography results. Furthermore, it substantially reduces back pressure and enables the accommodation of back pressure from detection equipment attached to the outlet lead. Furthermore, the simple design of flying lead section can substantially reduce wear and tear thereof and therefore substantially increase the reliability of this component.

In prior art counter current chromatography instruments, the gear sets have been open, necessarily so by the design of the instruments. This has caused difficulties in lubrication of the gear sets because of the loss of lubricant during use of the machine, the spoiling of the internal casing of centrifuge, making the centrifuge difficult to operate, and also has caused such centrifuges to be noisy in operation. The design of the enclosed gear set taught herein can substantially reduce the above-mentioned problems and can provide for carefully controlled lubrication of the rotor mechanism for a bobbin, thereby providing much more reliable rotation of the bobbin.

The bobbin structure taught herein enables easy removal of the bobbin, even by the user. Previously, any change of the coils had to be carried out by a service engineer and not by the instrument user. Now, it will be possible for a user to change bobbins, for example to replace an old bobbin with an equivalent new bobbin, and also for a user to have several different designs of bobbin with different coil configurations, thereby enabling a user for the first time to use a single centrifuge for different experimentation.

Moreover, the preferred design of bobbin taught herein enables an end user to see the ends of the coils, where the stationary phases occur. Such viewing can either be done by the naked eye or by automated optical equipment allowing automated detection and analysis from viewing the coil during operation of the centrifuge. This can provide a very significant advantage in such instruments. For example, a user may wish to include within the mixture being centrifuged optical (such as florescent) markers which become visible during the separation process. Such markers could be detected either by the naked eye or, for example, by a CCD camera and suitable processing software for processing the image from the CCD camera to determine the areas within the coil where the florescent markers become visible.

Other advantages of the teachings herein will be apparent from the following specific description.

BRIEF DESCRIPTION OF DRAWINGS

Embodiments of the present invention are described below, by way of example only, with reference to the accompanying drawings, in which:

FIGS. 6a to 6d show different examples of possible internal coil cross-sectional shapes.

DETAILED DESCRIPTION OF THE PREFERRED EMBODIMENT

Figure 1:
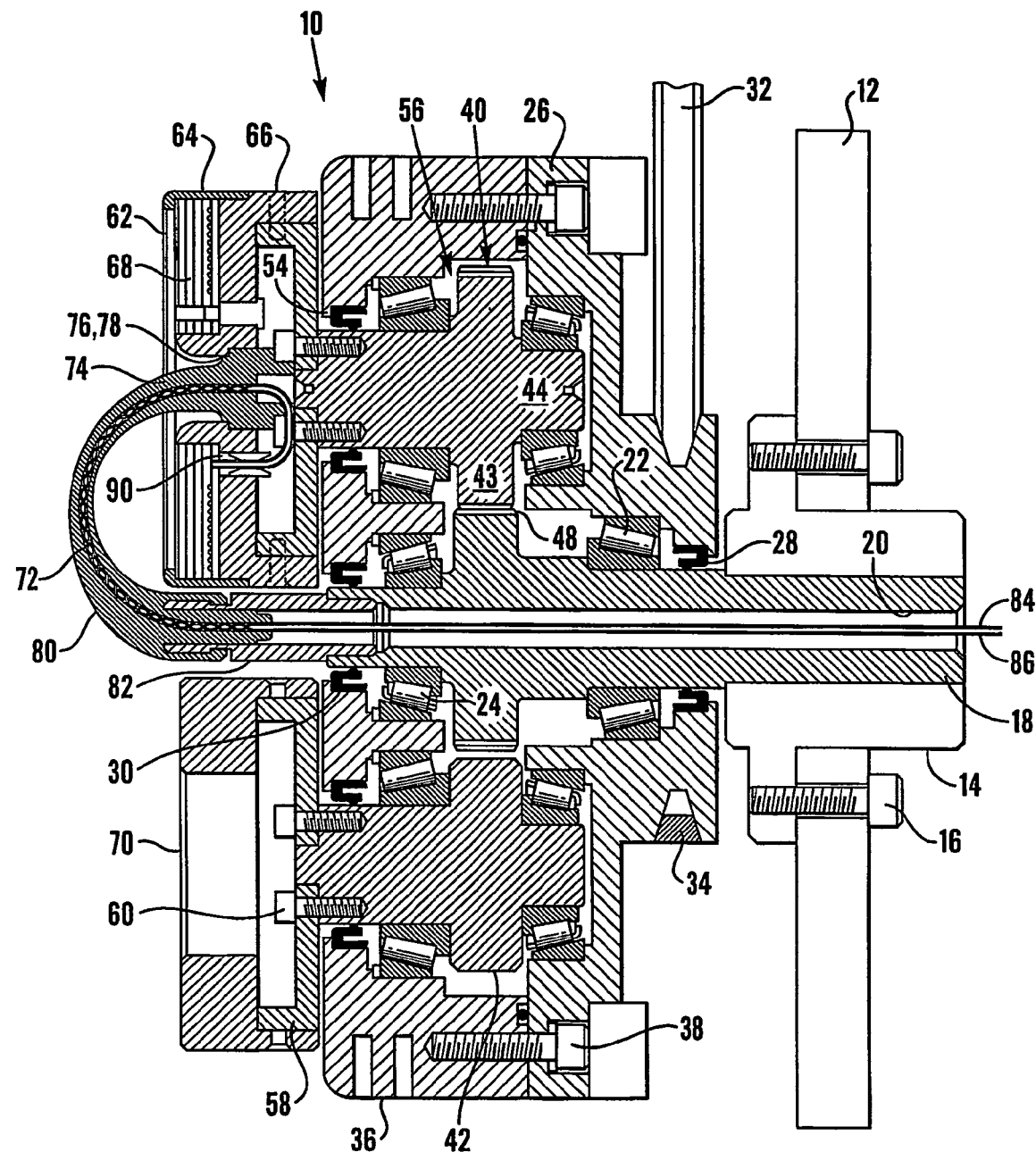
FIG. 1 is a schematic diagram in cross section of a preferred embodiment of counter-current chromatography apparatus.

Referring to FIG. 1, there is shown a preferred embodiment of a "J" type coil planet centrifuge 10 for counter current chromatography (CCC). The centrifuge 10 is intended to be suitable for use with small diameter coils, for example of 1 millimetre internal diameter or less, rotated at high speeds, for example in excess of 2000 rpm. Of course, the size of coil and rotational speeds can be chosen on the basis of the desired application.

The centrifuge 10 is typically kept in a casing (not shown) for protection purposes and for allowing control of environmental conditions such as temperature. Furthermore, in addition to the components shown in the Figure, the centrifuge 10 is provided with the other elements typical in apparatus of this type, such as power supplies, couplings to mass spectrometer equipment and so on, which will be immediately apparent to the skilled person and thus not described herein in detail.

The centrifuge 10 includes a support wall 12, in practice integral with the casing, to which is attached a mounting bush 14 by bolts or other suitable fastening means 16. The mounting bush holds a cantilever shaft 18 which in the described embodiment cannot rotate. The shaft 18 is provided with a central bore 20 for purposes described below.

Coupled to the cantilever shaft 18 by first and second sets of radial bearings 22, 24 is a rotor 26. The bearings 22, 24 are taper roller bearings in a preferred arrangement. First and second radial seals 28, 30 are provided to protect the bearings 22, 24 and contain lubricating oil.

Proximate the support wall 12 there is provided a drive belt 32 which drives a corresponding pulley 34 of the rotor 26 in conventional manner.

At a frontal portion of the rotor 26 there is provided a set of cooling fins 36 extending into the rotor 26.

It will be seen from FIG. 1 that the rotor 26 is formed in two parts secured together by bolts or other suitable fastening means 38 for assembly purposes.

The rotor 26 houses, in this embodiment, two enclosed gear sets 40, 42. Different embodiments may be provided with a different number of gear sets and/or with gear sets of different configuration.

Gear set 40 provides a bobbin rotor, as is described below, while gear set 42 is coupled to a counter-weight. Gear set 40 includes a planetary shaft 44 and rotatingly meshes with teeth 48 integral with shaft 18. First and second sets of bearings 50, 52 locate the planetary shaft 44 rotatably in the rotor 26. A seal 54 seals the gear set 40 in such a manner as to provide a chamber 56 within which the first gear set 40 and within which the planetary shaft 44 and bearings 50, 52 are located. As explained below, this chamber 56 is at least partially filled with lubricant such as oil or grease.

As can be seen in FIG. 1, the frontal bearings 52 are larger than the rear bearings 50 since the bearings 52 will take the load of the bobbin 62 or counter-weight 70, both of which are described below.

The second gear set 42 is substantially the same as the first gear set 40 although in this embodiment is not driven by the shaft 18 into rotation. The reason is that in this embodiment the second gear set 42 acts as or supports a counter-weight. There could be other embodiments of the counter-weight. In embodiments where it supports a second bobbin, it would be arranged to mesh with the teeth 48 of the shaft 18 to be rotated thereby.

The planetary shaft 44 of each gear set 40, 42 is provided with a bobbin or counter-weight mounting 58 fixed thereto by bolts or other suitable fastening means 60. To the mounting 58 of the first gear set shaft 44 there is attached a bobbin 62 formed of a coil housing 64 having an annular flange which fits around the outer perimeter of the mounting 58 and which includes a plurality of bores (in this case four) for receiving fixing bolts 66. In this manner, the bobbin is fixed to the mounting 58 and thus rotates with the rotatable shaft 44. It is envisaged that the bolts 66 could be replaced by a quick release coupling mechanism to allow for fast changing of the bobbin 62, for the purposes described herein. Similarly, a quick release mechanism could also replace bolts that hold mounting 58 to the shaft 44.

The bobbin housing 64 also holds the coil assembly 68 which may be of conventional form, may incorporate potted coils or a coil system of the type described below in connection with FIGS. 2 to 6. These Figures disclose a coil system in which at least a part of a conduit wall forming the coil is produced in a solid substrate, such as being machined as a recess in a disc of solid material. A plurality of such discs forms the coil assembly.

At the other side of the rotor 26, the counter weight 70 has a similar structure to the bobbin 62 and is designed to provide a balancing weight when the bobbin is in full use, as is known in the art. In this embodiment the counter-weight is free to rotate, although could be driven to rotate in the same manner as is the bobbin 62.

As can be seen in FIG. 1, the bobbin 62 is open at its centre, which opening provides for the placement of a flying lead section 72. A first end 74 of the flying lead section 72 is held in the bobbing 62 by mutually co-operating shoulders 76, 78. A second end 80 of the flying lead section 72 is coupled to the cantilever shaft 18 by a suitable non-rotatable bush 82, or a continuation of the cantilever shaft 18.

Located in the flying lead section 72 there are provided the inlet and outlet leads 84, 86 of conventional type. One end of each flying lead 84, 86 is coupled to the coil assembly 68 by a suitable coupling 90 (only one coupling 90 being visible in the Figure). The flying leads 84, 86 pass through the central bore 20 of the stationary cantilevered shaft 18 and in use are coupled to a mass spectrometer (not shown).

In this embodiment, the flying lead section 72 is in the form of a sheath of elastomeric material and the inlet and outlet leads 84, 86 are embedded therein, typically during the manufacturing process. Preferably, the leads 84, 86 are twisted around one another so as to follow substantially the same path when the machine is in use. Where more than two leads 84, 86 are provided these may be braided.

The sheath of the flying lead section 72 is preferably designed so as to retain a substantially semi-circular shape when the centrifuge 10 is in use. For this purpose, the dimensions of the sheath are such that it is more rigid at its end 80 relative to its end 74, typically by making the end 80 of greater cross-sectional diameter. In this manner, when the bobbin 62 rotates, producing an outward radial force on the flying lead section 72, the greater stiffness of the end 80 relative to the end 74 allows only partial deformation of the flying lead, designed to be such as to produce the semi-circular shape. The form of the sheath can be determined readily by experimentation or calculation following the teachings herein.

In the preferred embodiment, the inlet and outlet leads 84, 86 are of reduced diameter, typically 1 millimetre or less.

In one experimental embodiment, the centrifuge was provided with one driven planetary shaft 44 rotated about a 50 mm radius up to a maximum speed of 2,100 rpm. The coil 64 had a beta value range of 0.68 to 0.79, a volume of 4.6 ml using 0.76 mm bore tubing 10.15 metres long. The coil was serviced by a single pair of 0.5 mm bore PTFE inlet and outlet leads 84, 86 embedded in the flying lead section 72 in a simple 180° turn aligned with the "g" field produced on rotation of the rotor 26 and consequentially induced motion of the planetary shaft 44. This set up, with a mobile flow rate of up to 2 ml/min could achieve separation in 3 to 20 minutes, substantially faster than prior art systems and with a substantially reduced back pressure.

In use, the rotor 26 is rotated by the driving of drive belt 32 by the motor of the coil planet centrifuge. Such rotation is principally achieved as with prior art centrifuges but at the higher speeds disclosed herein.

The rotor 26 rotates around shaft 18 by virtue of the roller bearings 22, 24.

Engagement of the teeth 48 of the shaft 18 with those of the rotor shaft 44 cause rotation of this shaft 44 about its own axis and also, of course, about the axis of cantilevered shaft 18. This rotation of the shaft 44 causes an equivalent rotation of the bobbin and hence of the coils or bobbin assembly 68 fixed therewithin.

The counter weight 70 counters the eccentric load caused by rotation of the bobbin 62 so as to ensure that the rotor 26 is substantially balanced.

Mixture to be subjected to chromatography is fed in through inlet lead 84 with a pumped mobile solvent phase passing through the central bore 20 of cantilevered shaft 18, through the flying lead section 72 and therefrom into the inlet of coil 68. External pumping action causes this fluid to passes through coil 68 and thereby to undergo sequential mixing and settling with a stationary solvent phase being retained by coil rotation so as to separate as in conventional liquid-liquid chromatography.

At the end of the coil 68, the separated fluid then passes out through the outlet lead 86 directly to a detector, typically a mass spectrometer.

As explained above, the flying lead section 72 is designed such that during rotation of the rotor 26 it adopts a substantially semi-circular shape, achieved by making the end 80 thicker than the end 74. This profile minimises potential blockage and disturbance of fluid passing through the outlet lead 86. The twisting or braiding of the inlet and outlet leads 84, 86 ensures that each lead follows substantially a similar or the same profile as the other leads, to obtain reproducible results.

As with any moving component, heat is generated during use of the centrifuge and in particular at the bearings 52 at the frontal end of the shaft 44, caused by the load of bobbin 62. This heat is effectively managed in the described embodiment by the provision of lubricant in the chamber 56 which is retained at a level sufficient to contact and at least partially cover the bearings 52. Heat is thus transferred from the bearings 52 into the lubricant and therefrom into the casing of the rotor 26.

The cooling fins 36 in the rotor casing 26 assist in expelling heat from the rotor 26. As will be apparent from the Figure, the cooling fins 36 are located at a distance from the front face of the rotor 26 and thus at a certain distance from the bobbin 62. In this manner, heat is in effect directed away from the bobbin 62 and away from the fluid being centrifuged within the coils 68, thus having a stabilising effect on the fluid temperature.

The feature of enclosing the gear sets 40, 42 within the rotor 26 substantially reduces the noise of the instrument. Furthermore, it provides a closed chamber for the lubricant, ensuring efficient use of lubricant and thus more reliable operation of the rotor shaft 44 and also avoids the splattering and loss of lubricant as experienced with the prior art machines.

The level of lubricant within the chamber 56 of the rotor 26 is preferably always maintained sufficient to cover at least partially being bearings 52. For this purpose, there is provided in the preferred embodiment a viewing window (not shown) into the chamber 56 so that a user can see the amount of lubricant in the chamber.

The rotor 26 is preferably provided with an inlet conduit to the chamber 56, although it is also possible to replenish this chamber 56 by inserting a needle between the seals 54 and the outer periphery of the rotor shaft 44.

As explained above the coil assembly 68 is preferably substantially all made of transparent or translucent material such that movement of fluid within the coil 68 can be seen looking at the bobbin 62 face on (looking from the left hand side in the Figure). As the coil 68 is typically of spiral configuration, the ends of each coil winding will be visible to a user and thereby the stationary phase is secured within the coil 68. It is possible with this arrangement also to provide for automatic viewing such as by a CCD camera linked to analysis equipment able to analyse the progress of chromatography within the coils 68. A suitable mechanism will be apparent to the skilled person.

A user is also able to replace the bobbin 62 relatively easily, for example to replace the bobbin 62 with a new equivalent bobbin or with a bobbin having a different coil structure. In order to achieve this, the user need only withdraw the end 80 of flying lead section 72, which is typically a push fit within the bore 20 of shaft 18, and unscrew the radial screws 66 (of which four are preferably provided) to remove the coil housing 64 of bobbin 62. The flying lead section 72 can then be fed through the central aperture in the bobbin 62, withdrawing its end 80 and bushing 82 last (these will pass through the central bore of the bobbin 62) for use with a new bobbin; alternatively a new set of flying leads can be supplied with each new bobbin. A pair of removable connectors 90 (for example, screw threaded) are provided to connect the leads 84, 86 to the ends of the coil 68. A new bobbin is then attached to flying leads 84, 86 and then attached to the mounting 58 by the fixing bolts 66.

In the preferred embodiment, the bolts 66 are replaced by quick release catches to make replacement of the bobbin 62 even faster.

Thus, the user is able to replace the bobbin 62 with relative ease and need not be required to call out skilled service personnel for this purpose.

It can be seen from the above disclosure that the preferred embodiment provides the least stressful path for the flying lead section 72 and a simple arrangement of the cantilevered rotor driving the single planet shaft with the bobbin mounted on the end of the shaft in a cantilevered fashion.

Furthermore, the ability to see the flying lead section 72 enables an operator to see the state of this section of the inlet and outlet leads and replace it as and when necessary. The section 72 is completely unsupported and has no surface which touches the bobbin or other component, adding to the section's durability.

The section 72 in effect provides potting of the inlet and outlet leads 84, 86, reducing back pressure levels compared to prior art machines and also prevents twisting of the leads in a manner which could cause malfunction of the instrument.

Figure 2:
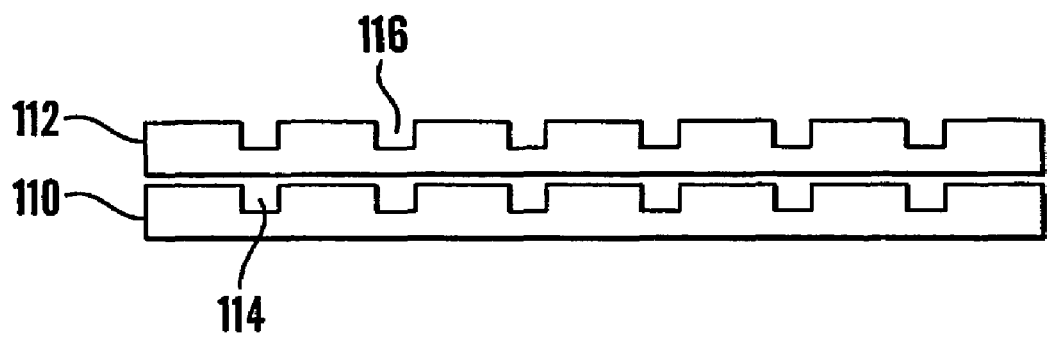
FIG. 2 is a schematic view in cross-section of an embodiment of coil assembly.

Referring now to FIG. 2, the preferred embodiment of coil assembly is formed from a plurality of rigid substrates 110, 112 which are typically disc-shaped in plan view.

The substrates 110, 112 can be made from a variety of materials, such as glass, ceramic, PTFE, FEP or other such machinable or mouldable material.

Produced within each substrate 110, 112, in this embodiment, there is a channel 114, 116 which is closed by the lower surface of a substrate lying thereon, as shown in relation to channel 114. Not shown in FIG. 2 is a coupling conduit for coupling the two channels 114, 116 together to form a unitary coil. However, as described below, the structure can provide for a plurality of separate coils within the substrates 110, 112.

Although only two substrates 110, 112 are shown, there are typically provided more to provide several or many substrate layers and one or more coils having several windings provided by the channels 114, 116. As with the two substrate layer example shown in FIG. 1, the winding of each substrate layer 110, 112 is coupled to the winding(s) of the immediately adjacent layer(s) by one or more suitable conduits to form a single coil. Nevertheless, in some applications a single coil winding provided by a single channel 114, 116, may be desired. In practice, the number of coil windings provided is dependant upon the total length of coil desired.

In some embodiments, there may be provided in each substrate 110, 112 a plurality of channels 114, 116 which couple separately to an equivalent number of channels 114, 116 in adjacent substrate layers 110, 112 to provide a plurality of separate coils. These coils may have the same form but may also be different, as will be apparent from the disclosure below.

The substrates 110, 112 are secured together to ensure that the channels 110, 112 are sealed, apart from at their ends. Any suitable sealing method may be used, typically being dependant upon the material chosen for the substrates 110, 112. Examples include bonding by a bonding agent, friction welding and heat welding.

The channels 114, 116 may be formed in any suitable manner and similarly this is dependant upon the material of the substrate 110, 112 and the manner of their formation. For example, the channels 114, 116 could be formed by machining, during moulding of the substrates 110, 112 (for example by lost wax moulding), by etching, by laser cutting or by any other suitable method.

Figure 3:
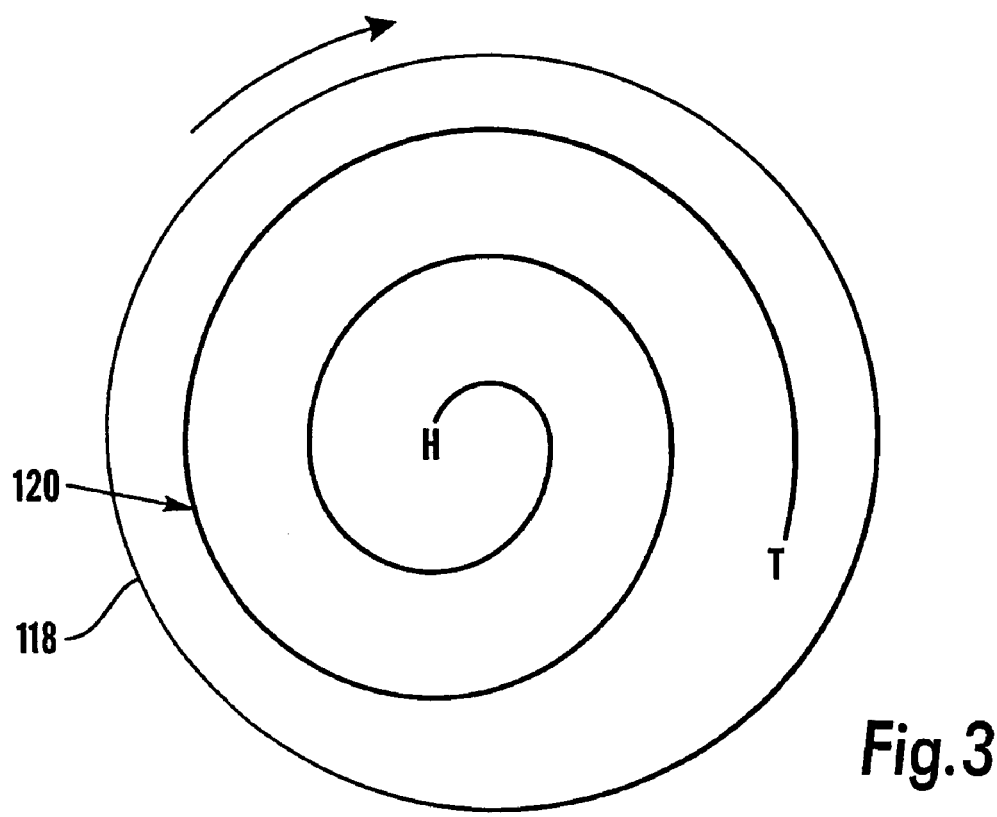
FIG. 3 is a plan view of a part of the coil assembly of FIG. 2.
Figure 4:
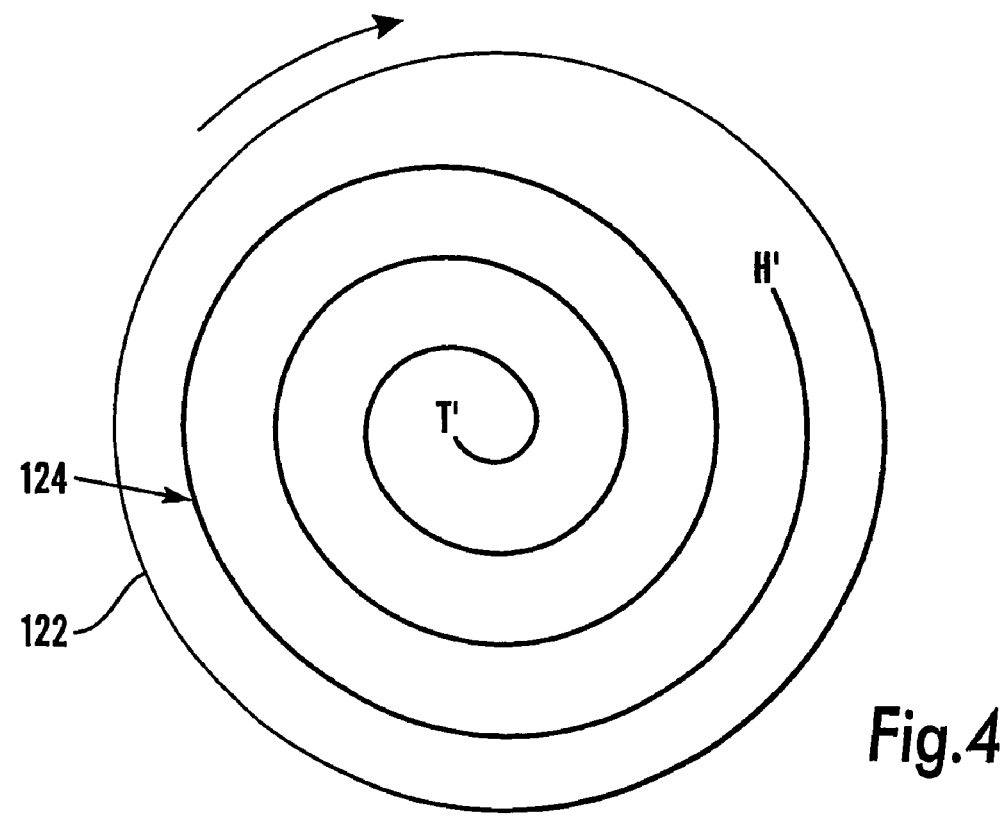
FIG. 4 is a plan view of a part of another embodiment of coil assembly.

Referring now to FIG. 3, there is shown in plan view an example of substrate 118 with a channel 120 which provides a spiral winding outwardly in a clockwise direction from its head end H to its tail end T and suitable for clockwise rotation of the substrate 118. FIG. 3 provides a mirror image of the winding 20 by having a channel 24 formed in a substrate 122 which provides a spiral winding inwardly in a clockwise direction from its head end H' to its tail end T'.

The substrates 118, 122 are designed to be placed one on top of the other and for their channels to be connected together by a short conduit (not shown). It will be apparent to the skilled person that this conduit will be much shorter that the conduit which would be necessary in conventional coil systems, providing significant operational advantages.

Figure 5A:
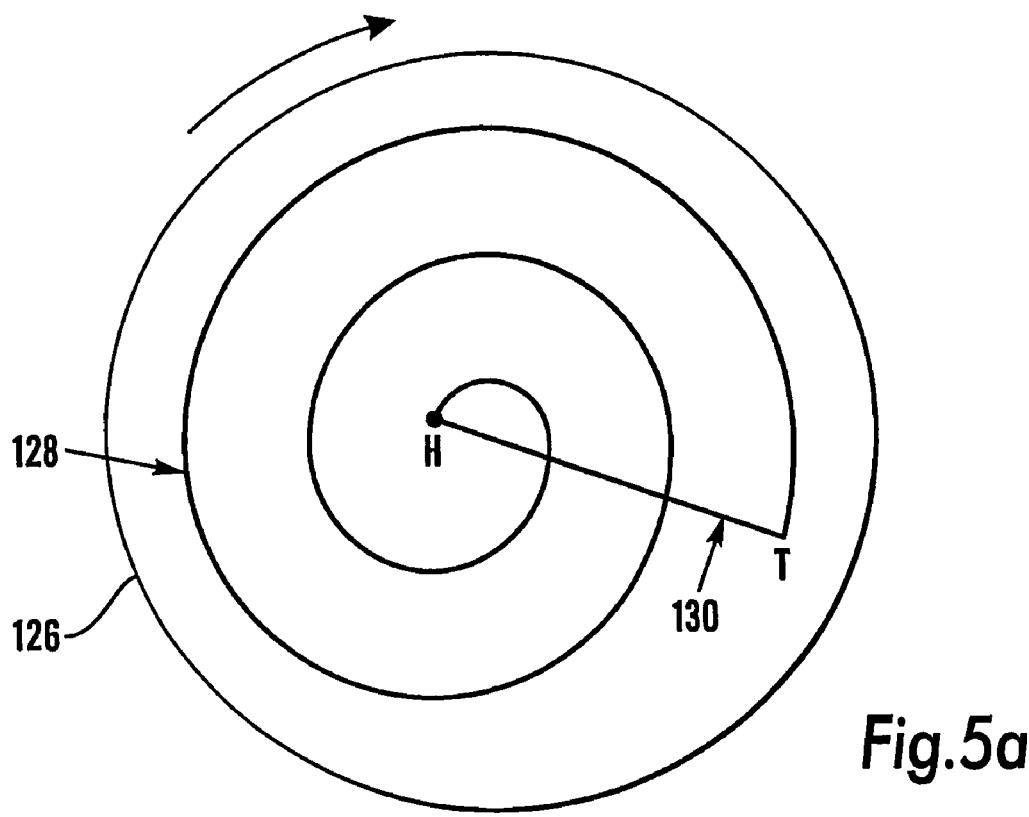
FIGS. 5a and 5b are two plan views of coil windings and coupling conduits for coupling the two windings together.
Figure 5B:
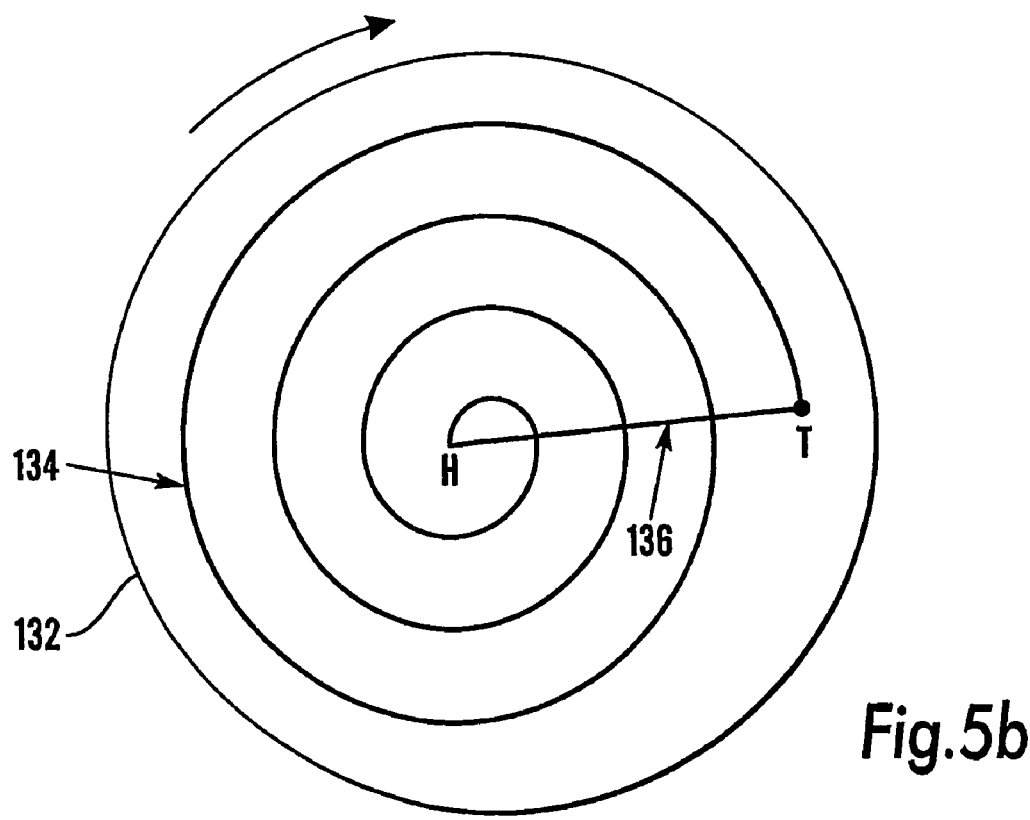

FIGS. 5a and 5b show an alternative substrate 126, 132 and channel 128, 134 arrangement in which the channels 128, 134 are identical to one another and are provided with coupling conduits 130, 136 respectively. In the example shown, the coupling conduit 30 couples the two channels 128, 134 together while the coupling conduit 136 is provided to coupled the channel 34 to a channel of an overlying substrate or, if at the end of the coil, to an inlet/outlet lead.

The coupling conduits 130, 136 can easily be formed in the substrates 126, 132, for example in the side opposite that in which the channels 128, 134 are formed, with a suitable bore connecting the coupling conduits to their channels.

With conventional coils formed from tubing, the internal shape of the tubing is typically limited to being round. However, with this invention, it is possible to provide any suitable cross-sectional shape for the internal wall(s) of the channels. FIGS. 6a to 6d show various examples of cross-sectional shape. Of course, these shapes may be provided by recesses on one or both of the abutting faces of adjoining substrates.

FIG. 6a shows a conventional circular shape while FIG. 6b shows a square shape. FIG. 6c shows a channel cross-sectional shape which is rectangular and oriented at an angle of around 45° to the horizontal. This shape provides a relatively wide surface for supporting the stationary phases.

FIG. 6d shows another example of channel cross-section.

The cross-sectional shape of the channels and their orientation can be chosen as desired by the skilled person and will be relatively easy to manufacture. Furthermore, the internal channel shape need not be uniform throughout a channel. In some applications, for example, it may be advantageous to provide changing internal channel shapes to influence the behavior of the chromatography phases, to promote mixing and so on. For these purposes, there may be provided surface roughness, baffles and the like.

Although the examples described above, and shown in the drawings, provide uniform coils, the system can provide for different coil forms. For example, a channel in one substrate can be wound at a first pitch while a channel in an adjoining substrate can be wound at a different pitch. Similarly, the pitch of any one channel winding can be varied. It is also possible to provide uneven curvature of a channel to generate pockets for stationary phases. Furthermore, this type of coil structure can provide constant helix spirals, double or treble start parallel spirals for multiple coils (indeed even more than three starts if desired) and variable and enhanced helix angle coils. The specific set-up is at the choice of the designer.

Once the various substrate layers are bonded or welded together, they provide a coil structure which is very rigid and very solid. Furthermore, it is possible to produce coils with substantially lower coil volume than with conventional tube coils, as it is possible to produce coils with much higher coil volume. The structure is very stable and can be rotated at very high speeds much in excess of 2000 rpm without risk of deformation of the coil structure.

Furthermore, in the preferred embodiment the substrates 110, 112 are formed of transparent or translucent material so that the interior of the channels 114, 116 is visible from outside the assembly. This can enable a user to see the effect of the centrifuging on a fluid within the coil. They also lend themselves to automatic optical detection, for example through a CCD camera

The invention claimed is:

1. A countercurrent chromatography apparatus comprising a centrifuge including a drive rotor for driving the rotated components of the centrifuge, at least one coil arranged to be rotated by the drive rotor, a rotor body having rotor bearings and heat transfer means including a heat sink fitted to or integral with the body and having cooling fins a distance from a front face of the drive rotor operable to transfer heat from the rotor body and away from the coil.

2. A centrifuge according to claim 1, wherein the heat sink includes a plurality of cooling elements in the rotor body.

3. A centrifuge according to claim 2, wherein the cooling elements are cooling fins formed in the body.

4. A centrifuge according to claim 2, wherein the cooling elements are arranged to direct heat away from the centrifuge coil or coils.

5. A centrifuge according to claim 1, wherein the rotor body includes an enclosed bearing chamber enclosing the rotor bearings.

6. A centrifuge according to claim 5, wherein the heat transfer means is arranged to dissipate heat generated by the rotor bearings.

7. A centrifuge according to claim 5, wherein the heat transfer means are cooling fins formed in the body.

8. A centrifuge according to claim 7, wherein the cooling fins are formed in the body adjacent to the rotor bearings.

9. A countercurrent chromatography apparatus comprising a centrifuge including a drive rotor for driving the rotated components of the centrifuge, at least one coil arranged to be rotated by the drive rotor, a rotor body and heat transfer means including a heat sink fitted to or integral with the body and having cooling fins a distance from a front face of the drive rotor operable to transfer heat from the rotor body and away from the coil, wherein the rotor body includes an enclosed bearing chamber enclosing rotor bearings and the heat transfer means is arranged to dissipate heat generated by the rotor bearings.

10. A centrifuge according to claim 9, wherein the cooling elements comprise cooling fins formed in the body adjacent to the rotor bearings.

* * * * *